United States Patent [19]

Dupuis et al.

[11] Patent Number: 5,553,630

[45] Date of Patent: Sep. 10, 1996

[54] USE OF METAL OXIDE NANOPIGMENTS FOR PROTECTING HAIR KERATIN AGAINST ATMOSPHERIC ATTACK, ESPECIALLY LIGHT, METHOD OF PROTECTING HAIR AND GEL COMPOSITION USING THESE NANOPIGMENTS

[75] Inventors: Christine Dupuis, Paris; Claude Dubief, Le Chesnay, both of France

[73] Assignee: L'Oreal, Paris, France

[21] Appl. No.: 157,093

[22] PCT Filed: Jun. 2, 1992

[86] PCT No.: PCT/FR92/00486

§ 371 Date: May 9, 1994

§ 102(e) Date: May 9, 1994

Related U.S. Application Data

[63] Continuation of WO92/21315, Dec. 10, 1992.

[30] Foreign Application Priority Data

Jun. 4, 1991 [FR] France ...................... 91 06745

[51] Int. Cl.$^6$ ...................................... A61K 7/06
[52] U.S. Cl. .......................... 132/202; 424/70.1
[58] Field of Search ................... 132/202, 209; 424/70.1, 70.9

[56] References Cited

U.S. PATENT DOCUMENTS 4,551,330  11/1985  Wagman et al. ............ 424/70.1 X
5,240,695  8/1993  Dubief et al. ............... 424/70.9 X

FOREIGN PATENT DOCUMENTS 0200839  11/1986  European Pat. Off. .
2184356  6/1987  United Kingdom .
9006103  6/1990  WIPO .
9011067  10/1990  WIPO .

OTHER PUBLICATIONS

Schlossman, M., "Treated Pigments. New Ways to Impart Color on the Skin", Cosmetics & Toiletries, vol. 105, Feb. 1990, pp. 53–64.

Patent Abstracts of Japan, vol. 13, No. 461, Oct. 18, 1989.

Patent Abstracts of Japan, vol. 13, No. 336, Jul. 27, 1989.

Griebler, W., "Titandioxid—ein anorganischer Rohstoff in der Kosmetik", Seifin, Ole, Fette, Wachse, vol. 113, No. 20, Dec. 10, 1987, pp. 765–771.

*Primary Examiner*—Robert P. Swiatek
*Attorney, Agent, or Firm*—Jacobson, Price, Holman & Stern, PLLC

[57] ABSTRACT

Use of metallic oxide nanopigments selected from titanium, zinc, cerium and zirconium or blends thereof, having an average size of less than 100 nm and preferably 5 and 50 nm, to preserve the hair's mechanical properties and especially its strength and elasticity, and protect it against external influences and especially sunlight. The quantity of metallic oxide nanopigments used in a non-rinsed cosmetic support is between 0.2 and 2% by weight. The invention also concerns cosmetic compositions for hair in the form of gel.

27 Claims, No Drawings

USE OF METAL OXIDE NANOPIGMENTS FOR PROTECTING HAIR KERATIN AGAINST ATMOSPHERIC ATTACK, ESPECIALLY LIGHT, METHOD OF PROTECTING HAIR AND GEL COMPOSITION USING THESE NANOPIGMENTS

The present invention concerns the use of metal oxide nanopigments for protecting hair keratin against atmospheric attack, especially light, a method of protecting hair and a gel composition using these metallic oxide nanopigments.

It is well known that light attacks hair keratin. Several publications have demonstrated that natural light destroys certain aminoacids in the hair and, in changing the nature of hair fibre, reduces mechanical properties such as tensile strength, breaking stress and elasticity.

Tensile strength can be measured using the 15% extension level. This is the force which must be applied to a wet strand of hair of a given length to lengthen it permanently by 15%. The higher the force required, the stronger and more elastic is the strand.

Polyaminoamides (French patent FR-A-2 599 968) and light filtering substances such as 2-hydroxy-4 -methoxybenzophenone-5-sulfonic acid and its salts (French patent FR-A-2 627 085) or 4-(2-oxo-3-bornilydene methyl)benzene sulfonic acid and its salts (European patent application No 0 329 032) have been suggested to protect hair keratin against attack by light.

It has surprisingly been discovered by the applicant that metal oxide nanopigments of titanium, zinc, cerium or zirconium with an average diameter of less than 100 nanometers, in particular between 5 and 50 nanometers, can preserve the hair's mechanical properties, especially tensile strength and elasticity, against their degradation by light. This property has been revealed by exposure to natural light (sunny environment) and to artificial light (xenon emitter of a SUNTEST HANAU accelerated ageing apparatus).

The present invention therefore consists in the use of metal oxide nanopigments of titanium, zinc, cerium or zirconium or mixtures thereof for protecting the mechanical properties of hair, in particular tensile strength, against degradation by atmospheric attack, in particular by light.

The term "nanopigments" means pigments with an average diameter of less than 100 nanometers, preferably between 5 and 50 nm.

The metal oxides may be coated or uncoated.

Coated pigments are pigments which have been chemically, electronically, mechanochemically and/or mechanically surface treated with compounds such as those described in Cosmetics & Toiletries 1990, Vol 105, February 1990, p 53–64, for example amino acids, beeswax, fatty acids, fatty alcohols, anionic surfactants, lecithins, sodium, potassium, zinc, iron or aluminum salts of fatty acids, sodium hexametaphosphate, metal (titanium or aluminum) alkoxides, polyethylene, silicones, proteins (collagen, elastin), alkanolamines, silicon oxides, and other metal oxides.

Particularly preferred coated pigments are titanium oxides coated with:

silica, such as SUNVEIL from IKEDA, silica and iron oxide, such as SUNVEIL F from IKEDA, silica and alumina, such as MT 500 SA and MT 100 SA from TAYCA and TIOVEIL from TIOXIDE, alumina, such as TIPAQUE TTO-55 (B) and TIPAQUE TTO-55 (A) from ISHIHARA and UVT 14/4 from KEMIRA, alumina and aluminum stearate, such as MT 100 T from TAYCA, alumina and aluminum laurate, such as MT 100 S from TAYCA, iron oxide and iron stearate, such as MT 100 F from TAYCA, zinc oxide and zinc stearate, such as BR 351 from TAYCA, silica, alumina and silicone, such as MT 600 SAS and MT 500 SAS from TAYCA, silica, alumina, aluminum stearate and silicone, such as STT-30-DS from TITAN KOGYO, alumina and silicone, such as TIPAQUE TTO-55 (S) from ISHIHARA, triethanolamine, such as STT-65-S from TITAN KOGYO, stearic acid, such as TIPAQUE TTO-55 (C) from ISHIHARA, sodium hexametaphosphate, such as MT 150 W from TAYCA.

Metal oxide mixtures containing equal weights of titanium oxide and cerium oxide coated with silica, such as SUNVEIL A from IKEDA, can also be cited.

Uncoated titanium oxides are sold by TAYCA under the trade names MT 500 B and MT 600 B, by DEGUSSA under the trade name P 25, by WACKHERR under the trade name "Transparent titanium oxide PW" and by MIYOSHI KASEI under the trade name UFTR, for example.

Uncoated zinc oxides are sold by SUMITOMO under the trade name ULTRA FINE ZINC OXIDE POWDER, by PRESPERSE under the trade name FINEX 25 and by IKEDA under the trade name MZO-25, for example.

Uncoated cerium oxide is sold by RHONE POULENC under the trade name COLLOIDAL CERIUM OXIDE, for example.

Mixtures of these pigments may also be used.

Coated or uncoated titanium oxide pigments are particularly preferred for use in the present invention.

In accordance with the invention, the quantity of nanopigments used for protecting the mechanical properties of hair against attack by light is preferably between 0.2 and 2% by weight, contained in a non-rinsed cosmetic support.

In accordance with a preferred embodiment of the invention, these nanopigments are used in a gelled cosmetic support. The following gelling agents can be used:

polyacrylic acids cross linked using a polyfunctional agent, particularly those sold by GOODRICH under the trade name CARBOPOL, such as Carbopol 910, 934, 934 P, 940, 941, 1342;

aqueous dispersions of ammonium acrylate/acrylamide copolymer (95/5 by weight), cross linked using a poyunsaturated olefinic reticulating agent, dispersed in a water-in-oil emulsion constituted by 30% by weight of said copolymer, 25% by weight of paraffin, 4% of a mixture of sorbitan stearate and a hydrophilic ethoxylated derivative, and 41% by weight of water, such as the emulsion sold by HOECHST under the trade name PAS 5161;

gels resulting from the ionic interaction of a cationic polymer constituted by a copolymer of cellulose or a cellulose derivative grafted with a hydrosoluble quaternary ammonium salt monomer and an anionic carboxylic polymer having an absolute capillary viscosity in dimethylformamide or methanol at a 5% concentration at 30° C. less than or equal to $30 \times 10^{-3}$ Pa.s, the gel itself having a modulus 3 Epprecht-Drage viscosity in 1% solution in water at 25° C. greater than or equal to 0.50 Pa.s.

These gels are described in French patent No 2 598 611.

The preferred product among these is that resulting from ionic interaction between a hydroxyethylcellulose copolymer grafted by a radical mechanism with a diallyl dimethylammonium chloride such as the product sold by NATIONAL STARCH under the trade name CELQUAT L 200 and a copolymer of methacrylic acid and methyl methacrylate having a capillary viscosity measured in 5% solution in dimethylformamide at 30° C. in the order of $15.10^{-3}$ Pa.s.

A particularly preferred product is that resulting from the ionic interaction between the hydroxyethylcellulose copolymer mentioned above and a cross linked methacrylic acid and ethyl acrylate copolymer sold by COATEX under the trade names VISCOATEX 538, 46 and 50.

Particularly preferred metal oxide nanopigments of the present invention are uncoated titanium oxides with a granulometry of 15 to 40 nanometers in a cosmetic support which is gelled using the hydroxyethylcellulose copolymer mentioned above associated with a copolymer of methacrylic acid and methyl methacrylate or preferably a cross linked copolymer of methacrylic acid and ethyl acrylate sold by COATEX under the trade names VISCOATEX 538, 46 and 50.

The present invention also consists in a cosmetic composition for hair in gel form.

Cosmetic compositions for hair in accordance with the invention for protecting hair against degradation by light contain as their active ingredient at least one metal oxide nanopigment of titanium, zinc, cerium or zirconium. They are in gel form and constitute non-rinse styling, perming or blow drying compositions.

The gelling agents mentioned above are used in compositions in accordance with the invention in proportions of between 0.1 and 30% by weight, preferably between 0.2 and 10% by weight, with respect to the total composition weight.

Cosmetic compositions for hair in accordance with the invention have a pH of between 2 and 11, preferably between 3 and 9.

Cosmetic compositions in accordance with the invention may also contain well known cosmetic agents providing that they do not themselves change the mechanical properties of the hair keratin.

The following additives or cosmetic agents may be present in cosmetic compositions in accordance with the invention, for example: non-ionic, anionic or cationic polymers, preservatives, oils, pH regulators, waxes, antifatting agents, sequestrating agents, perfumes, dyes, cationic surfactants, proteins, silicones and organic solvents.

Polymers which are most frequently used in these compositions for giving hold to the hair are nonionic polymers such as polyvinylpyrrolidones, copolymers of polyvinylpyrrolidone and vinyl acetate, and anionic polymers such as copolymers of vinyl acetate and an unsaturated carboxylic acid such as crotonic acid, copolymers resulting from copolymerisation of vinyl acetate, crotonic acid and an acrylic or methacrylic ester, copolymers resulting from copolymerisation of vinyl acetate, an alkoylvinyl ether and an unsaturated carboxylic acid and copolymers resulting from copolymerisation of vinyl acetate, crotonic acid and a vinyl ester of a long carbon chain acid or an allyl or methallyl ester of a long carbon chain acid. These polymers are used in concentrations of between 0.1 and 5% by weight with respect to the total composition weight.

The compositions are in aqueous form but may also contain other cosmetically acceptable solvents such as low alcohols, for example ethanol or isopropanol, glycerol, glycols or glycol ethers such as the monobutyl ether of ethyleneglycol, propyleneglycol, or the monoethylether or the monomethylether of diethyleneglycol, in proportions which do not affect gel formation.

The present invention also consists in a method of protecting hair keratin against atmospheric attack, in particular attack by light, consisting in applying to the hair an effective amount of at least one metal oxide nanopigment of titanium, zinc, cerium or zirconium in a cosmetic support, the application not being followed by rinsing.

The following are non-limiting examples of the invention.

EXAMPLE 1

A styling gel having the following composition was prepared:

| | |
|---|---|
| Titanium dioxide (diameter: 15 to 40 nanometers) sold by DEGUSSA under the trade name P 25 | 1 g |
| Copolymer of methacrylic acid and methyl methacrylate (50/50) | 0.7 g |
| Copolymer of hydroxyethylcellulose and diallyl dimethyl ammonium chloride sold by NATIONAL STARCH under the trade name CELQUAT L 200 | 0.7 g |
| Siliconised cationic polymer sold by DOW CORNING at a concentration of 35% AM under the trade name Cationic emulsion DC929 | 0.35 g AM |
| Copolymer of vinylpyrrolidine and quaternised dimethylaminoethyl methacrylate sold by GAF at 50% AM under the trade name GAFQUAT 734 | 0.1 g AM |
| 2-amino-2-methyl-propan-1-ol | qs pH 7.5 |
| Ethyl alcohol | 8.6 g |
| Perfume, preservative, dye | qs |
| Water | qsp 100 g |

EXAMPLE 2

A styling gel having the following composition was prepared:

| | |
|---|---|
| Titanium dioxide (diameter: 15 to 40 nanometers) sold by DEGUSSA under the trade name P 25 | 1 g |
| Cross linked polyacrylic acid sold by GOODRICH under the trade name CARBOPOL 940 | 0.45 g |
| Copolymer of vinylpyrrolidone and vinyl acetate (65/35) sold by GAF under the trade name PVP/VA S 630 | 1 g AM |
| Ethyl alcohol | 17.2 g |
| Triethanolamine | qs pH 7.5 |
| Water | qsp 100 g |

EXAMPLE 3

A styling gel having the following composition was prepared:

| | |
|---|---|
| Zinc oxide (diameter: 5 to 15 nanometers) sold by SUMITOMO under the trade name ULTRA FINE ZINC OXIDE POWDER | 1 g |
| Copolymer of methacrylic acid and methylmethacrylate (50/50) | 0.7 g |
| Copolymer of hydroxyethylcellulose and diallyl dimethyl ammonium chloride sold by NATIONAL STARCH under the trade name CELQUAT L 200 | 0.7 g |
| Siliconised cationic polymer sold by DOW CORNING at 35% AM concentration under the trade name Cationic emulsion DC 929 | 0.35 g AM |
| Copolymer of vinylpyrrolidone and quaternised | 0.1 g AM |

-continued

| | | |
|---|---|---|
| dimethylaminoethyl methacrylate sold by GAF at 50% AM under the trade name GAFQUAT 734 | | |
| 2-amino-2-methyl-propan-1-ol | qs | pH 7.5 |
| Ethyl alcohol | | 8.6 g |
| Perfume, preservative, dye | qs | |
| Water | qsp | 100 g |

EXAMPLE 4

A styling gel having the following composition was prepared:

| | | |
|---|---|---|
| Titanium dioxide (diameter: 15 to 40 nanometers) sold by DEGUSSA under the trade name P 25 | | 1 g |
| Cross linked copolymer of methacrylic acid and ethyl acrylate sold by COATEX at 30% AM under the trade name VISCOATEX 50 | | 2 g AM |
| Copolymer of hydroxyethylcellulose and diallyl dimethylammonium chloride sold by NATIONAL STARCH under the trade name CELQUAT L 200 | | 1 g |
| Siliconised cationic polymer sold by DOW CORNING at a concentration of 35% AM under the trade name Cationic emulsion DC 929 | | 0.3 g AM |
| Copolymer of vinylpyrrolidone and vinyl acetate (65/35) sold by GAF under the trade name PVP/VA S 630 | | 1 g AM |
| 0.1 g AM | | |
| 2-amino-2-methyl-propan-1-ol | qs | pH 7.5 |
| Perfume, preservative | qs | |
| Water | qsp | 100 g |

We claim:

1. Method of protecting the mechanical properties of hair, particularly its tensile strength and elasticity, against atmospheric attack, and in particular against light comprising applying to the hair 0.2 to 2% by weight of at least one metal atmospheric attack protecting oxide nanopigment selected from the group consisting of titanium, zinc, cerium and zirconium oxides having a diameter of less than 100 nanometers in a cosmetic support, said application not being followed by rinsing.

2. Method according to claim 1 wherein at least one nanopigment having a diameter of between 5 and 50 nanometers is applied to the hair.

3. Method according to claim 1 wherein the at least one nanopigment is a titanium oxide nanopigment.

4. Method according to claim 1 wherein the at least one nanopigment is at least one uncoated metal oxide nanopigment.

5. Method according to claim 1 wherein the at least one nanopigment is at least one coated metal oxide nanopigment which has been treated by one or more chemical, electronic, mechanochemical and/or mechanical surface treatment techniques with compounds selected from the group consisting of amino acids, beeswax, fatty acids, fatty alcohols, anionic surfactants, lecithins, sodium, potassium, zinc, iron and aluminum salts of fatty acids, sodium hexametaphosphate, metallic alkoxides, polyethylene, silicones, proteins, alkanolamines and silicon oxides.

6. Method according to claim 5 wherein the at least one nanopigment is at least one titanium oxide nanopigment which has been coated with a member selected from the group consisting of silica, alumina, triethanolamine, stearic acid, sodium hexametaphosphate, silica and iron oxide, silica and alumina, alumina and aluminum stearate, alumina and aluminum laurate, iron oxide and iron stearate, zinc oxide and zinc stearate, silica, alumina and silicone, silica, alumina, aluminum stearate and silicone and alumina and silicone.

7. Method according to claim 5 wherein the at least one nanopigment is silica coated titanium and cerium oxides.

8. Non-rinse cosmetic composition for hair in the form of a gel for protecting the hair against atmospheric attack, in particular against light, comprising 0.2 to 2% by weight of at least one metal oxide nanopigment selected from the group consisting of titanium, zinc, cerium and zirconium oxides having a diameter of less than 100 nanometers, in a gelled cosmetic support.

9. Cosmetic composition according to claim 8 which contains at least one nanopigment having an average diameter of between 5 and 50 nanometers.

10. Cosmetic composition according to claim 8 which contains a titanium oxide nanopigment.

11. Cosmetic composition according to claim 8 contains at least one uncoated metal oxide nanopigment.

12. Cosmetic composition according to claim 8 which contains at least one coated metal oxide nanopigment which has been treated by one or more chemical, electronic, mechanochemical and/or mechanical surface treatment techniques with compounds selected from the group consisting of amino acids, beeswax, fatty acids, fatty alcohols, anionic surfactants, lecithins, sodium, potassium, zinc, iron and aluminum salts of fatty acids, sodium hexametaphosphate, metallic alkoxides, polyethylene, silicones, proteins, alkanolamines and silicon oxides.

13. Cosmetic composition according to claim 12 which contains at least one coated metal oxide nanopigment selected from the group consisting of titanium oxides coated with silica, silica and iron oxide, silica and alumina, alumina, alumina and aluminum stearate, alumina and aluminum laurate, iron oxide and iron stearate, zinc oxide and zinc stearate, silica, aluminum and silicone, silica, alumina, aluminum stearate and silicone, alumina and silicone, triethanolamine, stearic acid and sodium hexametaphosphate.

14. Cosmetic composition according to claim 12 which contains a mixture of silica coated titanium and cerium oxides.

15. Cosmetic composition according to claim 8 which contains 0.1 to 30% by weight with respect to the total composition weight of gelling agents selected from the group consisting of polyacrylic acids cross-linked using a polyfunctional agent, aqueous dispersions of ammonium acrylate/acrylamide copolymer cross-linked using a polyunsaturated olefinic reticulating agent, dispersed in a water-in-oil emulsion constituted by 30% by weight of said polymer, 25% by weight of paraffin, 4% of a mixture of sorbitan stearate and a hydrophilic ethoxylated derivative and 41% by weight of water, and gelling agents forming gels resulting from the ionic interaction of a cationic polymer constituted by a copolymer of cellulose or a cellulose derivative grafted with a hydrosoluble quaternary ammonium salt monomer and an anionic carboxylic polymer having an absolute capillary viscosity in dimethylformamide or methanol at a concentration of 5% and at 30° C. less than or equal to $30 \times 10^{-3}$ Pa.s, said gels having a modulus 3 Epprecht-Drage viscosity in 1% solution in water at 25° C. greater than or equal to 0.50 Pa.s.

16. Cosmetic composition according to claim 15 which contains 0.2 to 10% by weight with respect to the total composition weight of gelling agents.

17. Cosmetic composition according to claim 8 which contains an uncoated titanium oxide nanopigment with a granulometry of between 15 and 40 nanometers in a cosmetic support gelled with a copolymer of methacrylic acid and methyl methacrylate associated with a copolymer of hydroxyethylcellulose grafted by a radical mechanism with diallyl dimethylammonium chloride.

18. Cosmetic composition according to claim 8 which contains an uncoated titanium oxide nanopigment with a granulometry of between 15 and 40 nanometers in a cosmetic support gelled by a cross linked copolymer of methacrylic acid and ethyl acrylate associated with a copolymer of hydroxyethylcellulosed grafted by a radical mechanism with diallyl dimethylammonium chloride.

19. Cosmetic composition according to claim 8 which further contains at least one cosmetic additive selected from the group consisting of non-ionic, anionic and cationic polymers, preservatives, oils, pH regulators, waxes, antifatting agents, sequestrating agents, perfumes, dyes, cationic surfactants, proteins, silicones and organic solvents.

20. Cosmetic composition according to claim 19 which contains non-ionic polymers selected from polymers or copolymers of vinylpyrrolidone or contains anionic polymers in concentrations of between 0.1 and 5% by weight with respect to the total composition weight.

21. Method for protecting hair keratin against atmospheric attack, especially against light, comprising applying to the hair 0.2 to 2% by weight of at least one metal atomspheric attack protecting oxide nanopigment selected from the group consisting of titanium, zinc, cerium and zirconium oxides having an average diameter of less than 100 nanometers, in a cosmetic support.

22. Method according to claim 21 wherein the diameter of the at least one metal oxide nanopigment is between 5 and 50 nanometers.

23. Method according to claim 21 wherein the at least one metal oxide nanopigment is a titanium oxide nanopigment.

24. Method according to claim 21 wherein the at least one metal oxide nanopigment is at least one uncoated metal oxide nanopigment.

25. Method according to claim 21 wherein the at least one metal oxide nanopigment is at least one coated metal oxide nanopigment which has been treated by one or more chemical, electronic, mechanochemical and/or mechanical surface treatment techniques with compounds selected from the group consisting of amino acids, beeswax, fatty acids, fatty alcohols, anionic surfactants, lecithins, sodium, potassium, zinc, iron and aluminum salts of fatty acids, sodium hexametaphosphate, metallic alkoxides, polyethylene, silicones, proteins, alkanolamines and silicon oxides.

26. Method according to claim 25 wherein the at least one metal oxide nanopigment is a titanium oxide nanopigment coated with a member selected from the group consisting of silica, silica and iron oxide, silica and alumina, alumina, alumina and aluminum stearate, alumina and aluminum laurate, iron oxide and iron stearate, zinc oxide and zinc stearate, silica and alumina and silicone, silica and alumina and aluminum stearate and silicone, alumina and silicone, triethanolamine, stearic acid and sodium hexametaphosphate.

27. Method according to claim 25 wherein the at least one metal oxide nanopigment is titanium and cerium oxide nanopigments coated with silica.

* * * * *